United States Patent [19]
Tweardy et al.

[11] Patent Number: 5,797,713
[45] Date of Patent: Aug. 25, 1998

[54] ORTHOPEDIC SUPPORT UNIT FASTENER

[75] Inventors: Lisa Anne Gravell Tweardy, Mt. Laurel, N.J.; George Emmer Moore, Jeffersontown, Ky.

[73] Assignee: The Jerome Group, Inc., Moorestown, N.J.

[21] Appl. No.: 799,307

[22] Filed: Feb. 13, 1997

Related U.S. Application Data

[62] Division of Ser. No. 438,748, May 10, 1995, Pat. No. 5,632,722.

[51] Int. Cl.$^6$ .............................. F16B 21/00; A61F 5/00
[52] U.S. Cl. .................... 411/339; 411/512; 411/908; 602/18
[58] Field of Search ................................. 511/338, 339, 511/508, 509, 510, 512, 353, 908; 602/18

[56] References Cited

U.S. PATENT DOCUMENTS

| | | | |
|---|---|---|---|
| 4,035,874 | 7/1977 | Liljendahl | 411/339 X |
| 4,518,297 | 5/1985 | Kraus | 411/512 X |
| 4,538,597 | 9/1985 | Lerman . | |
| 4,702,233 | 10/1987 | Omicioli . | |
| 4,724,747 | 2/1988 | Sturm et al. | 411/510 X |
| 4,805,273 | 2/1989 | Burke et al. . | |
| 4,861,208 | 8/1989 | Boundy | 411/510 X |
| 5,038,759 | 8/1991 | Morgenstern . | |
| 5,366,438 | 11/1994 | Martin, Sr. . | |

Primary Examiner—Neill R. Wilson
Attorney, Agent, or Firm—Ratner & Prestia

[57] ABSTRACT

A orthopedic support unit fastener composed of a female portion which is molded directly as part of an orthopedic support component such as a sternum brace and has reinforcing ridges extending between an outer ring and a central receptacle which receives a male portion.

3 Claims, 6 Drawing Sheets

ORTHOPEDIC SUPPORT UNIT FASTENER

This application is a division of U.S. application Ser. No. 08/438,748, filed May 10, 1995 now U.S. Pat. No. 5,632,722.

BACKGROUND OF THE INVENTION

1. Field of the Invention

This invention relates to orthopaedic cervical collars, particularly those used in the treatment, stabilization and therapy of cervical trauma.

2. Description of Related Art

Various types of cervical collars have been developed in treating conditions of the neck and cervical spine. Some of these collars are intended merely as support for whiplash and other such injuries where support for the head and neck is needed. The primary objective for the use of such a collar is to partially immobilize the head and neck, to maintain a desired spinal alignment, to provide support for the head, and to relieve any spasm or strain to which the neck muscles may be subjected by transmitting weight or force from the head to the shoulders or adjacent area.

Other collars are intended to be used where near complete immobilization of the head and neck are necessary such as in an EMS pre-hospital setting. There are a multitude of cervical collars intended to perform one or more of the above-mentioned functions.

U.S. Pat. No. 3,572,328 to John L. Bond describes an adjustable, flexible cervical collar designed for universal use by providing vertically adjustable movable sections displaceable relative to one another and to a base portion.

U.S. Pat. No. 2,911,970 to W. L. Bartles pertains to a cervical collar having two piece construction which allows for adjustment of the forward portion of the cervical collar. This allows for the use of a single collar by persons having different length necks as measured in the front of the person.

Other collars intended for partial or total immobilization are shown in U.S. Pat. No. 4,413,619 and Reissue No. 32,219 to Garth. Such collars are generally made by die-cutting plastic sheet material and attaching various pieces together to form a collar. Die cut collars have two specific problems.

The first problem with die cut collars relates to the flexibility of the material from which the collar is formed. The material selected must be flexible enough to conform to the neck and head of the patient, while being sufficiently rigid to maintain the head of the patient in a fixed, predetermined spatial relationship with the body of the patient.

The second problem with die cut collars, as with all die-cut materials, is that no matter how well the pieces may be designed, there is always waste involved between pieces die-cut from a sheet. There is also waste from holes cut in those pieces. Accordingly, it would be more economical if such a collar could be produced by injection molding.

Injection molding of cervical collars has been previously attempted. U.S. Pat. No. 5,038,759 to Morgenstern shows an injection molded cervical orthopaedic device. While this solves the second problem by minimizing the waste generated by die cutting collars, it does not address the first problem of physical characteristics of the material from which the collar is formed.

The material forming the collar must be sufficiently flexible to allow the collar to conform to the neck of the patient on which it is placed. Yet the collar must have sufficient rigidity to hold the patient's neck in a predetermined position and sufficient toughness to withstand continued use. Of course, in the case of injection molding, the material must also be injection moldable. Most injection moldable materials strong and tough enough to maintain the head of a patient in a predetermined position are too stiff to be useful as a material for a cervical collar. Even those materials which might be difficult to mold do not normally meet these conflicting criteria. Finally, the chosen material should cause a minimum of interference with x-rays, magnetic resonance imaging and other diagnostic procedures. Few or no materials can meet all of these demands in a conventional molded or die cut cervical collar.

SUMMARY OF THE INVENTION

The present invention provides a cervical collar preferably formed from a thermoplastic material, which includes flexibility enhancing openings which allow the collar to conform properly to the shape of a patient's neck. Most preferably, the collar is formed from linear low density polyethylene, which is an injection moldable material. The collar may be injection molded and include female portions of medical rivets molded directly into the collar.

DETAILED DESCRIPTION OF THE FIGURES

As previously explained, the selection of material for use in producing a cervical collar is very important. The material must be sufficiently rigid to hold the head of a patient in a predetermined position but sufficiently flexible to allow the collar to conform to the head of a patient. In a die cut collar, polyethylene and polypropylene are common choices as materials of construction, and any such commonly used material should perform well in the present invention.

The material selected for production of an injection molded collar according to the present invention is preferably a linear low-density polyethylene with a melt flow index of about 20. Material with a melt flow index of 50 was tested but the collar cracked after a few weeks of use. This demonstrates the need for careful selection of the material of construction of the collar and the demands which are normally placed on a collar. In this case, while the material was sufficiently stiff to maintain the head of the patient in a fixed, predetermined spatial relationship to the body of the patient, the material was too brittle to withstand use for more than a short period of time.

The particular material preferred for use in injection molded collars according to the present invention, is linear low-density polyethylene (LLDPE). In particular, Petrothene® GB564 linear low density polyethylene obtained from Quantum Chemical Corporation, Inc., VSI Division of Cincinnati, Ohio was used to produce collars according to the present invention.

LLDPE offers advantages over other resins which make it the desirable material for use in cervical collars generally and in injection molded cervical collars in particular. LLDPE is more x-ray transparent than high density polyethylene (HDPE). This is important since most cervical collar patients are trauma victims and x-rays must be taken for various reasons, including insuring the proper alignment of the cervical spine after application of a collar.

LLDPE is also less dense than HDPE, and more pliable. Thus, to obtain the same stiffness of collar, the use of LLDPE requires more material but produces a thicker collar which is less likely to cut into the skin of a patient wearing the collar. Further, LLDPE is more temperature tolerant than other materials and therefore performs better in non-ideal conditions such as those found in emergency situations. LLDPE also has no shape "memory," and therefore, even if a collar of LLDPE is not stored flat, it can be flattened and shaped correctly prior to use. It will conform correctly to the neck of a patient without stress from prior bending, regardless of prior storage conditions.

Figure 1:
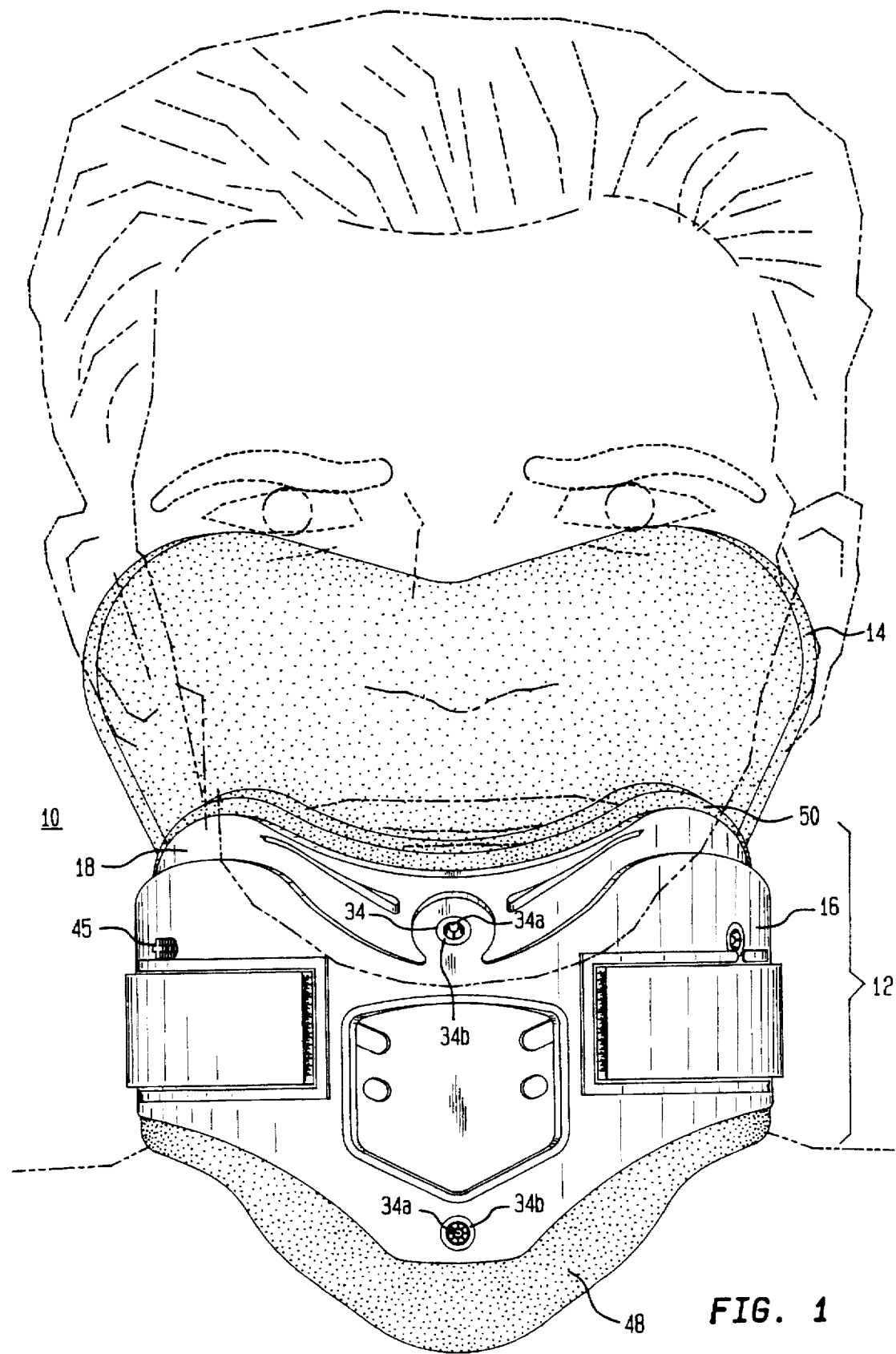
FIG. 1 is a front-view of the collar of the present invention secured to a patient.
Figure 2:
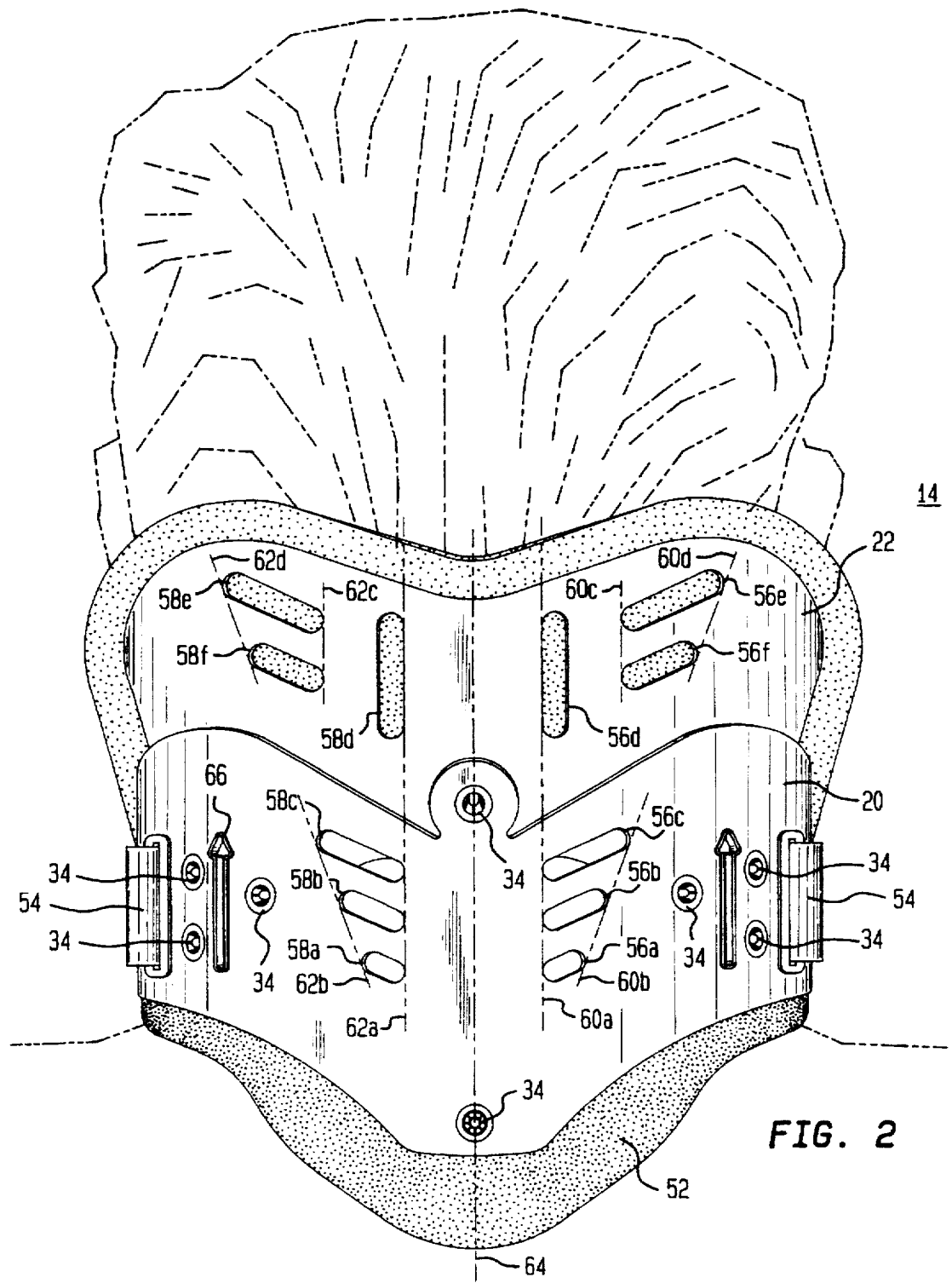
FIG. 2 is a rear-view of the collar of the present invention secured to a patient.
Figure 3:
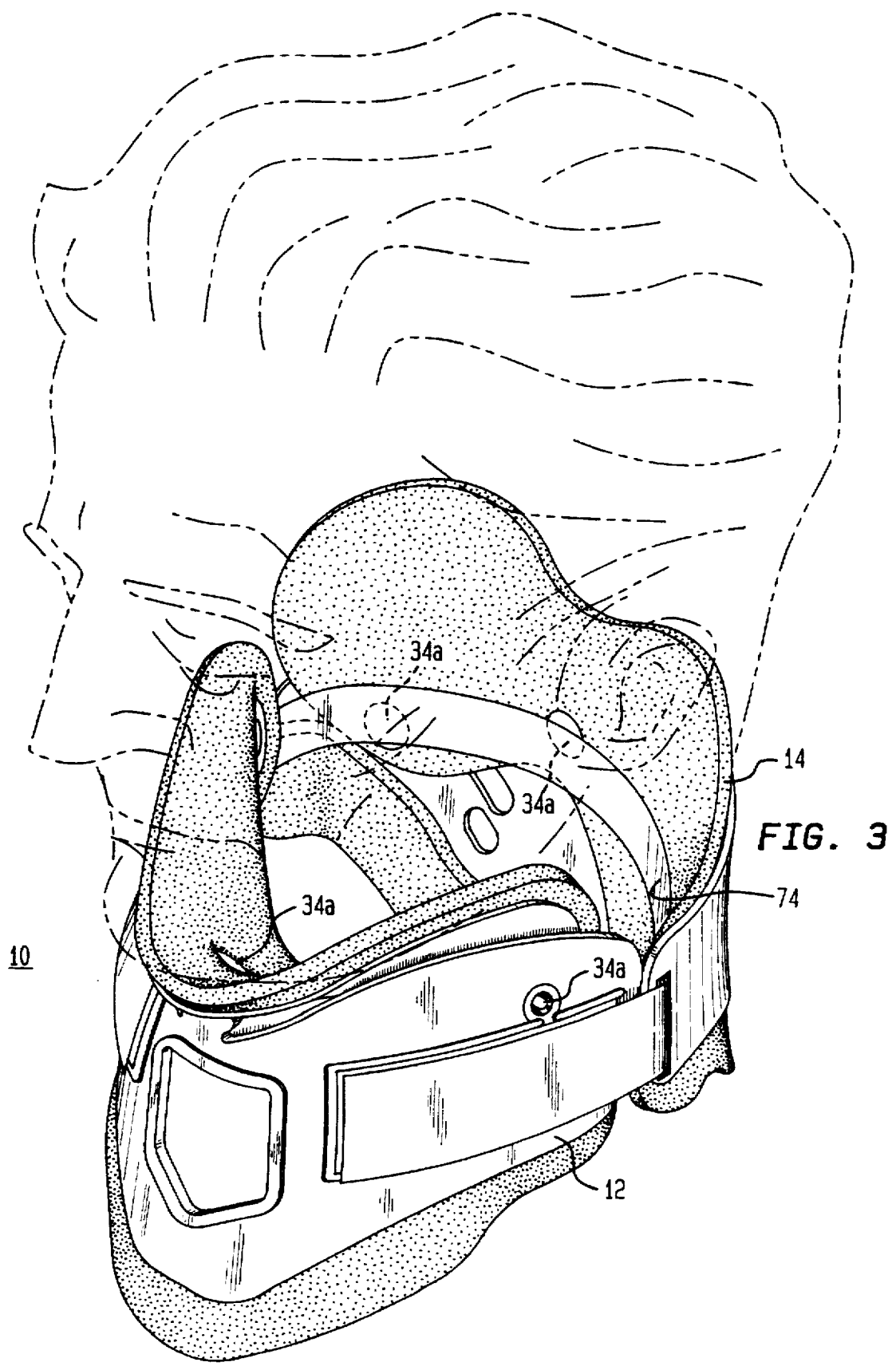
FIG. 3 is a perspective view of the collar of the present invention secured to a patient.

Referring now to FIGS. 1-3, cervical collar 10 comprises front semi-rigid portion 12 and rear semi-rigid portion 14. Front semi-rigid portion 12 comprises sternum brace 16 and jaw support 18. Sternum brace 16 may also be seen in FIG. 5, and jaw support 18 may also be seen in FIG. 4. The pieces of cervical collar 10 may be injection molded or die cut. Injection molding the pieces of a collar allows inclusion of structures which would be impossible or very difficult in die-cut structures.

Figure 5:
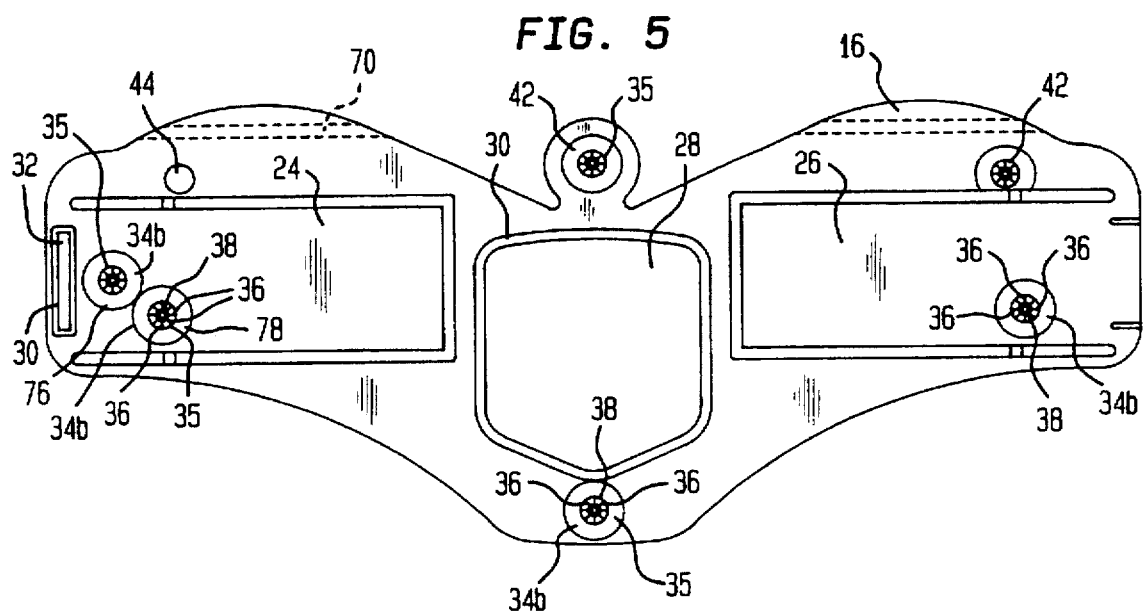
FIG. 5 is a plan-view of the front side of the front semi-rigid portion of the collar of the present invention.
Figure 6:
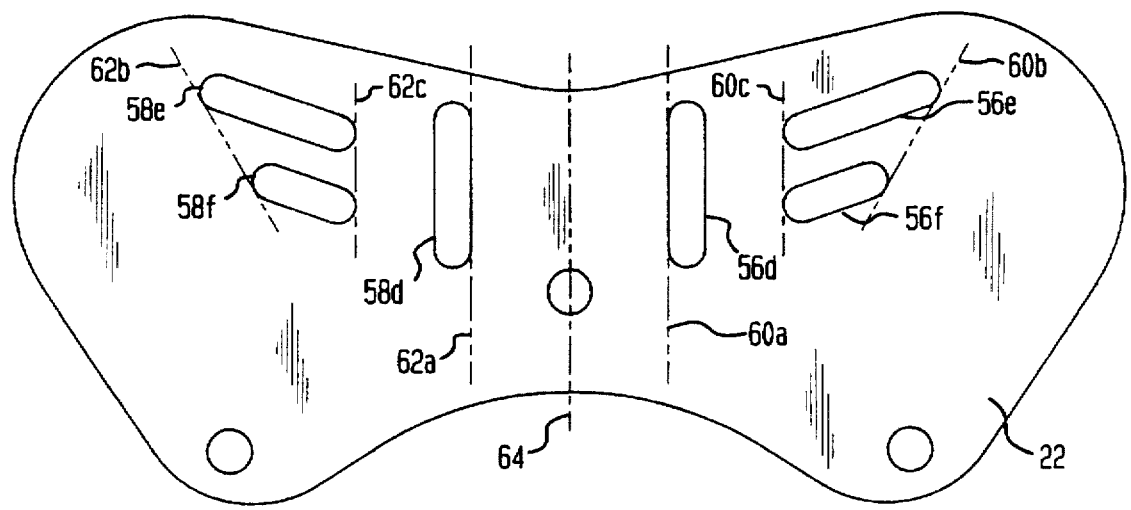
FIG. 6 is a plan-view of the occiput support of the collar of the present invention.
Figure 7:
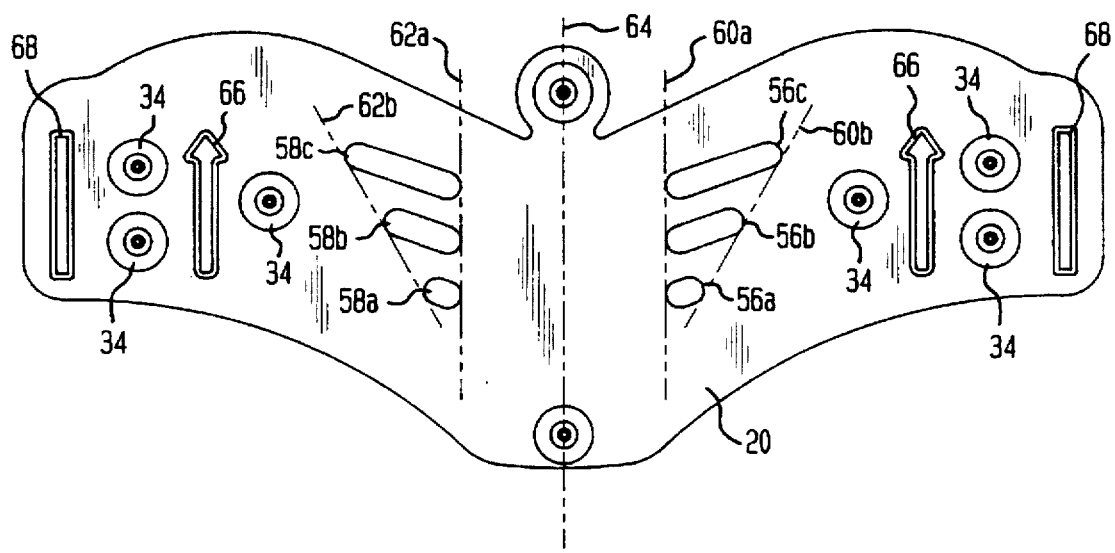
FIG. 7 is a plan-view of the rear semi-rigid portion of the collar of the present invention.

As can be seen from FIG. 5, sternum brace 16 includes two hook-and-loop fastener positioning guides, right positioning guide 24 and left positioning guide 26. As used herein, the terms "right" and "left" are defined as being from the point of view of a patient wearing the collar. Guides 24 and 26 each comprise a raised line around an area in which a loop portion of hook-and-loop fastener material 54 is to be applied. This aides in making certain the hook-and-loop fastener material is correctly placed on sternum brace 16. The inclusion of such a raised line would be difficult or impossible in a die-cut collar, but such a raised line is easily included in the injection molded collar of the present invention.

Sternum brace 16 also includes an opening 28 which allows access to the trachea of the patient should an emergency tracheotomy or other procedure need to be performed on the neck of a patient after the collar is in place. Opening 28 is reinforced around its periphery with a raised reinforcement rib 30. Opening 28 is also reinforced on the underside of sternum brace 16 by reinforcement ribs 31, as may be seen from FIG. 8. Sternum brace 16 includes hook-and-loop fastener guide 32 which also includes a raised reinforcement rib 30 around the periphery thereof.

The aforementioned features including guides 24 and 26 and raised reinforcement ribs 30 are included in the injection molded collar of the present invention. In a die cut collar, guides 24 and 26, as well as suitable reinforcements could be included by bonding extra layers of LLDPE onto sternum brace 16. Such a configuration is not shown in the figures hereof. Rather only the injection molded embodiment is depicted.

Figure 8:
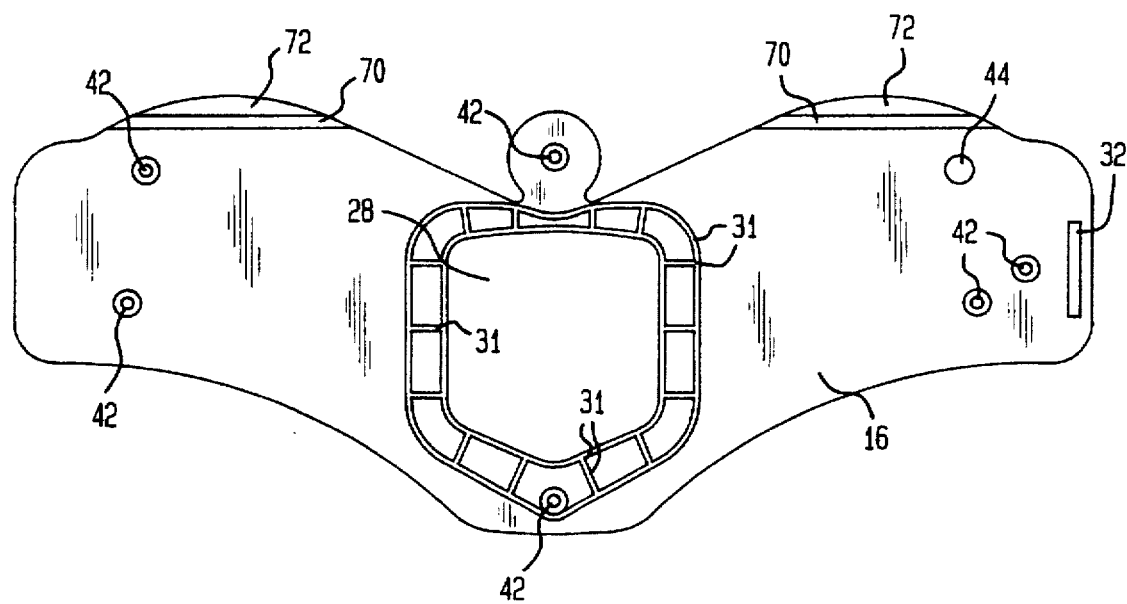
FIG. 8 is a plan-view of the rear side of the front semi-rigid portion of the collar of the present invention.

Further, sternum brace 16 includes a mandibular relief area 70. Mandibular relief area 70 is located on the inside of sternum brace 16, as shown in FIG. 8. Area 70 can be a straight depressed channel running across sternum brace 16. In an injection molded collar, the mandibular relief area 70 can be molded into sternum brace 16. In a die cut collar, area 70 could be formed by milling sternum brace 16. Of course, milling could be used on a molded collar as well, but molding area 70 directly into the collar would be more efficient.

Area 70 allows sternum brace 16 to conform more closely to the jaw line of a patient than would otherwise be possible. The area 70 is positioned such that it separates two upper portions 72 from the remaining (lower) portions of sternum brace 16. Area 70 acts as a hinge to allow upper portions 72 of sternum brace 70 to fold away from the patient to relieve pressure created by the collar along the jaw line (mandible) of a patient. This helps reduce discomfort to the patient and reduces the chance of the patient developing decubitus ulcers along the jaw.

Alternatively, area 70 may encompass not only a channel, but also the upper portions 72. Area 70 would then be a general weakening of the collar material throughout the area. Specifically, area 70 may begin with the full thickness of the collar and become thinner through upper portion 72, to the edge of sternum brace 16. Thus, the entire area 70 and 72 would be weakened and would allow flexibility.

Finally if the pieces of cervical collar 10 are injection molded, further advantages can be realized. For example, the injection molding of sternum brace 16 allows female portions of plastic rivets 34 to be integrally molded directly into sternum brace 16. Many modern cervical collars are secured together by means of plastic medical rivets (also called snap fasteners because they make a "snap" sound when joined). These rivets have male portion 34a and female portion 34b. Once the two portions are combined, it is difficult or impossible to non-destructively open the rivet. Hence these rivets are useful for assembling a cervical collar where permanency of attachment is desired. Further, the plastic rivets are desirable as they do not interfere with x-rays, magnetic resonance imaging, or other diagnostic techniques.

Heretofore, such plastic medical rivets have been molded separately and purchased by the manufacturer of the collar for use in assembling the collar. The use of injection molding allows female portions 34b of these rivets to be molded into the collar which saves production costs. Due to the shape of male portion 34a of rivet 34, specifically undercuts which provide locking strength to the rivet, molding the male portion of the rivet into the collar is not practical. Therefore, it is still necessary to produce male portion 34a of rivet 34 separately.

As can be seen from FIG. 5, female portions 34b of rivets 34 are molded directly into sternum brace 16. Since sternum brace 16 is formed from LLDPE, female portions 34b of rivets 34 are also formed from LLDPE. LLDPE is not as resistant to deformation as the material normally used for medical rivets. Therefore for rigidity and strength, female portion 34b has been designed to include reinforcing ridges 36 around circular central receptacle 38. Central receptacle 38 is a continuous ring of plastic with a hole in the middle. Central receptacle 38 receives male portion 34a of rivet 34. Reinforcing ridges 36 are straight ridges which extend from an outer ring 35 inwardly to receptacle 38 to reinforce central receptacle 38 and to add strength to female portion 34b of rivet 34. Generally, reinforcing ridges 36 are equally spaced about the circumference of central receptacle 38.

Figure 4:
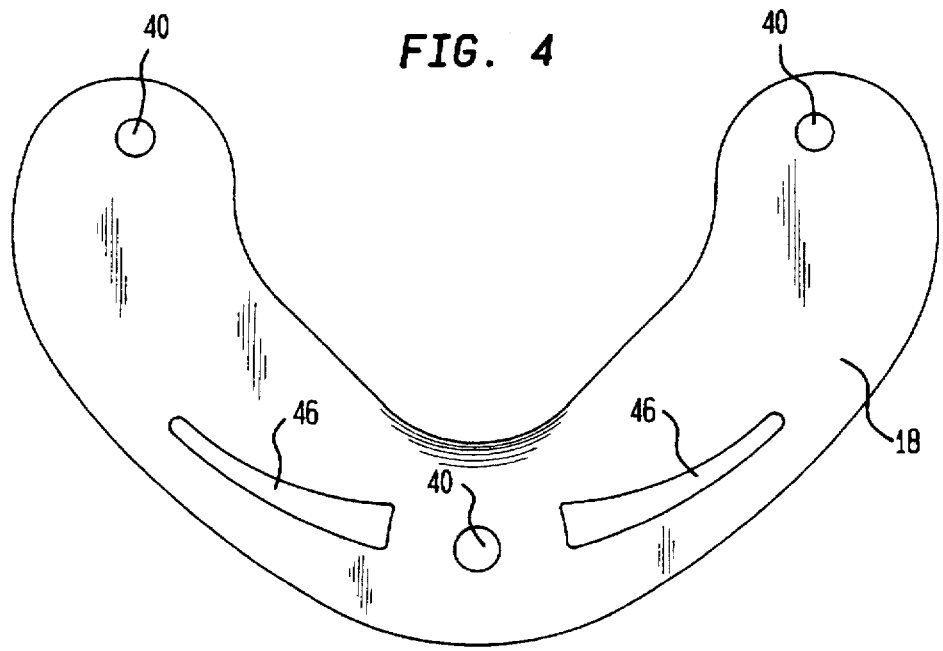
FIG. 4 is a plan-view of the jaw support of the collar of the present invention.

Jaw support 18 is attached to sternum brace 16 as shown in FIG. 4. Jaw support 18 includes attachment holes 40 for attachment to sternum brace 16. These are attached with rivets which fasten to sternum brace 16 at female rivet portions 42 which are identical to female rivet portions 34b previously described. The right-most attachment hole 40 (as viewed from the patient) aligns with attachment hole 44 on sternum brace 16. Attachment hole 44 receives a removable attachment stud which allows removeable attachment of the right-most portion of chin-support 18 to sternum brace 16. This removeable attachment is desired since the collars are generally shipped flat, and this removeable attachment allows the collar to be reflattened after use. Jaw support 18 also includes vent holes 46 which not only allow air and moisture to pass through jaw support 18 but also affect flexibility of the jaw support to allow it to contour to the shape of the chin of the user.

Rivets 34 are also used to attach sternum brace padding 48 to sternum brace 16. Jaw support padding 50 (as well as all other padding) may also be attached using rivets, or may be removably attached using hook-and-loop fasteners, snaps, buttons, or other removeable means of attachment. In this way, the padding can be washed or replaced as necessary.

Referring now to FIGS. 2, 3, 6 and 7, posterior support 20 includes molded in female rivet portions 34b. Plastic rivets 34 are used to hold posterior support padding 52 in place, as well as providing means for attaching hook-and-loop fasteners 54. Rivets 34 are also used for attaching occiput support 22 to posterior support 20.

As previously discussed, there are difficulties which arise when attempting to find a material with sufficient rigidity to hold the head of a patient in a fixed position, while conforming circumferentially to the neck of a patient. The same is true with the material used in the present invention, even though that material was chosen specifically for its properties in this regard. Accordingly, to add circumferential flexibility to the collar, several openings 56a–f and 58a–f have been added to posterior support 20 and occiput support 22. These openings are useful in adjusting the circumferential flex of the material whether the collar is injection molded or die cut.

As can be seen from FIG. 2, openings 56a, 56b, and 56c are arranged in a group, each having one end along a group line 60a. Similarly, openings 58a, 58b, and 58c are also arranged in a group with one end along a group line 62a. Both group lines 60a and 62a are vertical when a patient wearing the collar is in a seated or standing position.

As can also be seen from FIG. 2, openings 56a, 56b, and 56c are arranged such that a second end of each opening not on group line 60a is positioned along a second group line 60b. Group line 60b extends at an angle, from the bottom of posterior support 20 near group line 60a, at an angle up and away from group line 60a, and away from a vertical axis of symmetry 64. Similarly, openings 58a, 58b, and 58c are arranged with a second end along a second group line 62b which also angles up and away from axis of symmetry 64, but on the opposite side thereof from group line 60b.

Occiput support 22 also includes openings. Openings 56d, 56e, and 56f are located on the right side of occiput support 22. Openings 58d, 58e, and 58f are located on the left side of occiput support 22. When rear semi-rigid portion 14 is assembled, openings 56d and 58d fall along group lines 60a and 62a respectively. Openings 56e and 56f are arranged such that a first end of each opening falls along a third group line 60c which is vertically arranged. The second end of each opening falls on a further group line 60d. Openings 58e and 58f are also arranged such that a first end of each opening falls on group line 62c, and a second end falls on a group line 62d. Group lines 60d and 62d may optionally be aligned with group lines 60b and 62b.

Posterior support 20 and occiput support 22 are symmetrical about vertical axis of symmetry 64 which passes through the horizontal centers of both posterior support 20 and occiput support 22. Openings 56d and 58d are arranged along lines 60a and 62a respectively, and are arranged vertically, that is they are longer in the vertical than the horizontal direction.

Each of openings 56a–c and 58a–c are arranged with a first end of each opening nearest vertical axis of symmetry 64 resting along group lines 60a and 62a respectively. Each opening extends from group line 60a or 62a away from axis of symmetry 64. Each opening also has the second end of the opening resting on second group line 60b or 62b. Openings 56a–c and 58a–c are arranged neither vertically nor horizontally, but extend at an angle away from lines 60a and 62a respectively. Openings 56a–f and 58a–f are all oblong and of varying sizes. Although such openings work well in the collar of the present invention, these openings may also be round or all of one size and configuration and still achieve the same function by employing a sufficient number in an effective arrangement.

The openings therefore form V-shaped areas between group lines 60a and 60b, and between group lines 62a and 62b. Since material has been removed from posterior support 20 and occiput support 22 in these V-shaped areas, posterior support 20 and occiput support 22 will preferentially bend in these areas when force is applied. This allows the rear portion of the collar to conform more closely to the head of a user.

Also adding to the flexibility of posterior support 20 are vertical openings 66. As may be seen in FIGS. 2 and 7, vertical openings 66 are shaped like arrows, to show a user which side of the collar should be positioned on top when applied to a patient. However, the openings serve the function of increasing the flexibility of posterior support 20 to allow it to conform to the neck of the patient. Vertical openings 66 are placed near the ends of posterior support 20, which allows those ends to flex more than the center of posterior support 20.

Posterior support 20 also includes hook-and-loop fastener openings 68. Hook-and-loop fastener 54 is secured to posterior support 20 by rivets 34 located between vertical openings 66 and hook-and-loop fastener openings 68. The hook-and-loop fasteners 54 extend through hook-and-loop fastener openings 68 as may be seen from FIG. 2. This allows some of the force on hook-and-loop fasteners 54 to be transferred directly to posterior support 20, to relieve some of the force placed on rivets 34 by fasteners 54. Hook-and-loop fasteners 54 hold the collar in place and can therefore receive considerable force which must be transferred to collar 10.

Since the collar of the present invention is formed in two pieces, a front semi-rigid portion 12 and a rear semi-rigid portion 14, securing the collar to a patient can be difficult. Accordingly, collar 10 has been provided with a retaining strap 74. Retaining strap is an elastic strap which attaches to sternum brace 16 at rivets 76 and 78. When the collar is to be applied to a patient, the retaining strap 74 is placed loosely around the neck of the patient and fastened by hook and loop fasteners in area 26. Retaining strap 74 holds front semi-rigid portion 12 loosely in place until rear semi-rigid portion 14 can be attached. Once rear semi-rigid portion 14 is attached, retaining strap 74 remains in place, but performs no further function.

It is understood that various other modifications will be apparent to one skilled in the art without departing from the spirit and scope of this invention. Accordingly, it is not intended that the scope of the claims appended hereto be limited to the description as set forth herein, but rather that the claims be construed as encompassing all the features of patentable novelty that reside in the invention, including all features that would be treated as equivalents thereof by those skilled in the art to which this invention pertains.

What is claimed:

1. A joint in an orthopedic support unit comprising:

a first orthopedic support component;

a female rivet portion molded into said first orthopedic support component and having:
 (a) a circular outer ring,
 (b) a circular central receptacle, and
 (c) a plurality of straight reinforcing ridges extending between said circular outer ring and said circular central receptacle;

a second orthopedic support component; and a male rivet portion having an end oversized relative to said circular central receptacle of said female rivet portion and extending through said second orthopedic support component into said circular central receptacle of said female rivet portion for a press fit engagement with said female rivet portion.

2. A joint in an orthopedic support unit according to claim 1 wherein said reinforcing ridges are equally spaced around the circumference of said central receptacle.

3. A joint in an orthopedic support unit according to claim 1 wherein said orthopedic support unit is a cervical collar, said first orthopedic support component is a sternum brace, and said second orthopedic support component is a jaw support.

* * * * *